(12) United States Patent  (10) Patent No.: US 12,138,360 B2
Jang  (45) Date of Patent: Nov. 12, 2024

(54) PORTABLE STERILIZER

(71) Applicant: Pal Soo Jang, Daejeon (KR)

(72) Inventor: Pal Soo Jang, Daejeon (KR)

( * ) Notice: Subject to any disclaimer, the term of this patent is extended or adjusted under 35 U.S.C. 154(b) by 0 days.

(21) Appl. No.: 17/797,338

(22) PCT Filed: Jul. 20, 2022

(86) PCT No.: PCT/KR2022/010567
§ 371 (c)(1),
(2) Date: Mar. 1, 2024

(87) PCT Pub. No.: WO2023/043033
PCT Pub. Date: Mar. 23, 2023

(65) Prior Publication Data
US 2024/0189469 A1  Jun. 13, 2024

(30) Foreign Application Priority Data
Sep. 16, 2021  (KR) .......... 10-2021-0123586

(51) Int. Cl.
*A61L 2/20* (2006.01)
*A61L 2/22* (2006.01)

(52) U.S. Cl.
CPC ............ *A61L 2/202* (2013.01); *A61L 2/22* (2013.01); *A61L 2202/15* (2013.01); *A61L 2202/16* (2013.01)

(58) Field of Classification Search
CPC ........ A61L 2/202; A61L 2/22; A61L 2202/15; A61L 2202/16
See application file for complete search history.

(56) References Cited

U.S. PATENT DOCUMENTS 6,029,911 A * 2/2000 Watanabe ......... B01F 25/31242
261/DIG. 42
2004/0096354 A1  5/2004 Nomura et al.

FOREIGN PATENT DOCUMENTS

| KR | 2004-55796 | B1 | 9/2011 |
| KR | 10-2015-0063633 | A | 6/2015 |
| KR | 20-0482450 | Y1 | 1/2017 |
| KR | 10-2019-0029267 | A | 3/2019 |
| KR | 10-2292847 | B1 | 8/2021 |

* cited by examiner

*Primary Examiner* — Sean E Conley
(74) *Attorney, Agent, or Firm* — Goldilocks Zone IP Law

(57) ABSTRACT

A portable sterilizer includes a housing in which a water tank is installed inside and a nozzle capable of spraying sterilizing water in a fog state is installed to be exposed to an outside on a side thereof, an ozone gas supply unit installed inside the housing and configured to supply ozone gas to the nozzle, a compressed air supply unit installed inside the housing and configured to supply compressed air to the nozzle, and a water supply unit installed inside the housing and configured to supply water from the water tank to the nozzle. The ozone gas and compressed air are supplied to the nozzle in a mixed gas state, the water is supplied directly to the nozzle, and the mixed gas and water are finally mixed inside the nozzle and then sprayed with sterilizing water in a fog state.

5 Claims, 3 Drawing Sheets

PORTABLE STERILIZER

CROSS-REFERENCE TO PRIOR APPLICATIONS

This application is a National Stage Patent Application of PCT International Patent Application No. PCT/KR2022/010567 (filed on Jul. 20, 2022) under 35 U.S.C. § 371, which claims priority to Korean Patent Application No. 10-2021-0123586 (filed on Sep. 16, 2021), which are all hereby incorporated by reference in their entirety.

BACKGROUND

The present disclosure relates to a portable sterilizer and, more particularly, to a portable sterilizer that can spray ozone-containing sterilizing water in a fog state.

In recent years, there has been a growing awareness of global epidemics associated with new (novel) viruses such as coronavirus SARS-COV-2 identified in 2019. It is known that infection caused by a coronavirus can be effectively prevented to a large extent through basic preventive measures including hand washing as well as wearing a mask.

A sterilizer is made portable and is used for disinfection of factories, buildings, houses, etc., for spray disinfection of arable lands such as fruit orchards and vegetable fields, and livestock quarantine purposes for pig farms, dairy farms, poultry farms, etc.

Workers can load the sterilizer on a vehicle or cart, or hold or carry the sterilizer by themselves to perform control and quarantine work.

Such sterilizers may be categorized into various classes according to operating method, use, size, and the like. That is, since the size, shape, spray area of the particles to be sprayed in a free or granular form need to vary depending on the use for household, agricultural, or industrial, etc. and the spray target, various types of sprayers are required.

Meanwhile, in the case of a sterilizer for quarantine or sterilization, a sprayer with a particle size of several tens to several hundred μm is preferred because it is advantageous in terms of the prevention effect to distribute the chemical evenly over a wider area.

As described above, sterilizers mainly used for quarantine and disinfection are often called chemical liquid sprayers, quarantine devices, sterilization devices, etc.

Conventional sterilizers have been proposed as ultraviolet (UV) sterilizers that sterilize using the UV rays, chemical liquid sterilizers that sterilize using specific chemicals, etc.; however, these sterilizers have a problem in that they are not effective in dealing with coronaviruses.

Therefore, there is a need for a portable sterilizer that is easy to carry and can contribute to combating coronaviruses using ozone.

DOCUMENTS OF RELATED ART

Patent Documents (Patent Document 1) Korean Patent No. 10-2292847 (Aug. 18, 2021)
(Patent Document 2) Korean Utility Model Registration No. 20-0482450 (Jan. 18, 2017)

SUMMARY

The present disclosure has been made keeping in mind the problems occurring in the related art. An objective of the present disclosure is to provide a portable sterilizer that can quickly sterilize indoor objects and areas exposed to coronavirus SARS-COV-2 by spraying ozone-containing sterilizing water in a fog state.

The objectives of the present disclosure are not limited to those mentioned above, and other objectives not mentioned will be clearly understood by those skilled in the art to which the present disclosure pertains from the following description.

In order to achieve the above mentioned objective, according to an embodiment of the present disclosure, there is provided a portable sterilizer, including: a housing in which a water tank is installed inside, and a nozzle capable of spraying sterilizing water in a fog state is installed to be exposed to an outside on a side thereof; an ozone gas supply unit installed inside the housing and configured to supply ozone gas to the nozzle; a compressed air supply unit installed inside the housing and configured to supply compressed air to the nozzle; and a water supply unit installed inside the housing and configured to supply water from the water tank to the nozzle, wherein the ozone gas and compressed air may be supplied to the nozzle in a mixed gas state, the water may be supplied directly to the nozzle, and the mixed gas and water may be finally mixed inside the nozzle and then sprayed with sterilizing water in a fog state.

The housing may further include a Y-shaped mixing tube connected to the nozzle, wherein the ozone gas supply unit may be connected to a first branched side of the Y-shaped mixing tube, the compressed air supply unit may be connected to a second branched side of the Y-shaped mixing tube, and the ozone gas and compressed air may be mixed by the Y-shaped mixing tube and supplied to the nozzle as a mixed gas.

The ozone gas supply unit may include: an air pump; an ozone generator that generates ozone gas by mixing the air and ozone generated by the air pump; and an ozone gas supply hose connected to the first branched side of the Y-shaped mixing tube to supply the ozone gas generated by the ozone generator to the nozzle.

The compressed air supply unit may include: a compression pump; and a compressed air supply hose connected to a second branched side of a Y-shaped mixing tube to supply the compressed air generated by the compression pump to the nozzle.

The water supply unit may include: a water supply hose configured to connect the water tank and the nozzle; and an electric valve installed on the water supply hose and configured to regulate a flow of water supplied from the water tank to the nozzle.

The portable sterilizer may further include: a power supply unit for supplying power to the ozone gas supply unit, the compressed air supply unit, and the water supply unit, wherein the power supply unit may be composed of a controller and a battery.

The nozzle may be configured to as an atomizing nozzle so as to mix the mixed gas and water.

According to the present disclosure, by spraying ozone-containing sterilizing water in a fog state, it is possible to quickly sterilize and disinfect surfaces, indoor objects, and large areas exposed to coronavirus SARS-COV-2.

DETAILED DESCRIPTION

Hereinafter, preferred embodiments of the present disclosure will be described in detail with reference to the accompanying drawings. However, in describing the present disclosure, descriptions of already known functions or configurations will be omitted in order to clarify the gist of the present disclosure.

Figure 1:
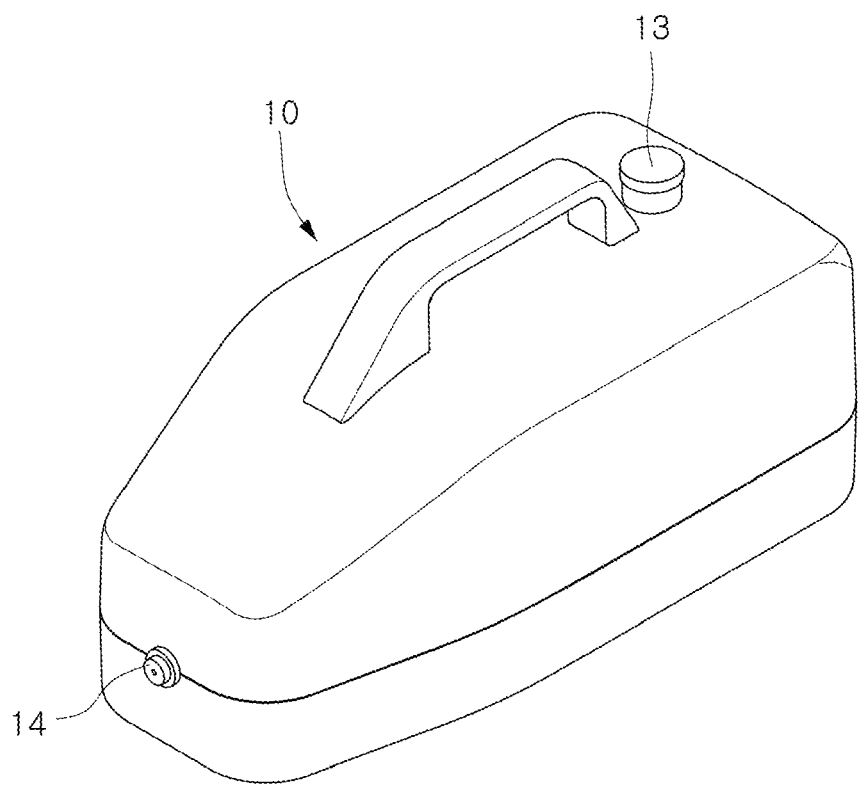
FIG. 1 is a perspective view showing a portable sterilizer according to the present disclosure.
Figure 2:
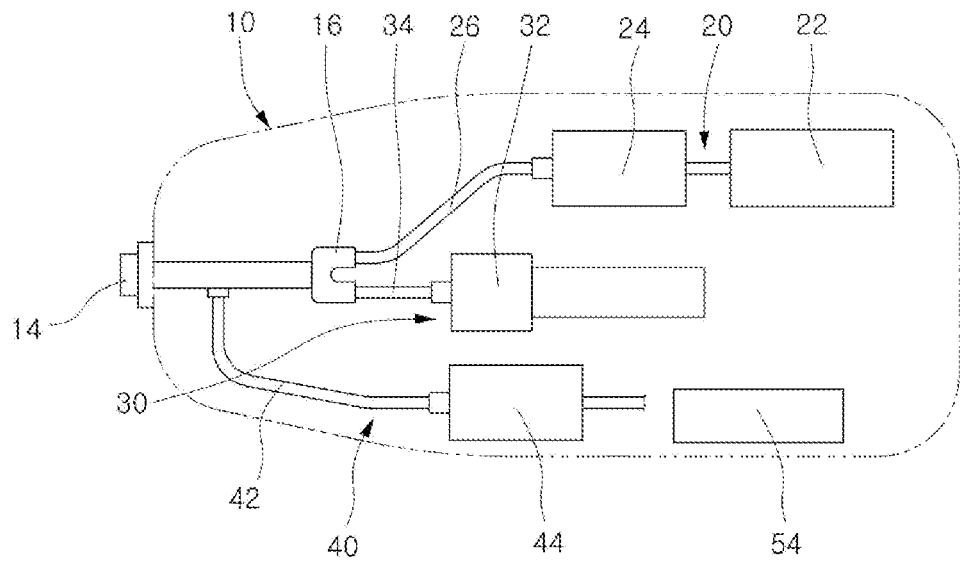
FIG. 2 is a plan view showing a state in which a water tank is removed from the inside of the portable sterilizer according to the present disclosure.
Figure 3:
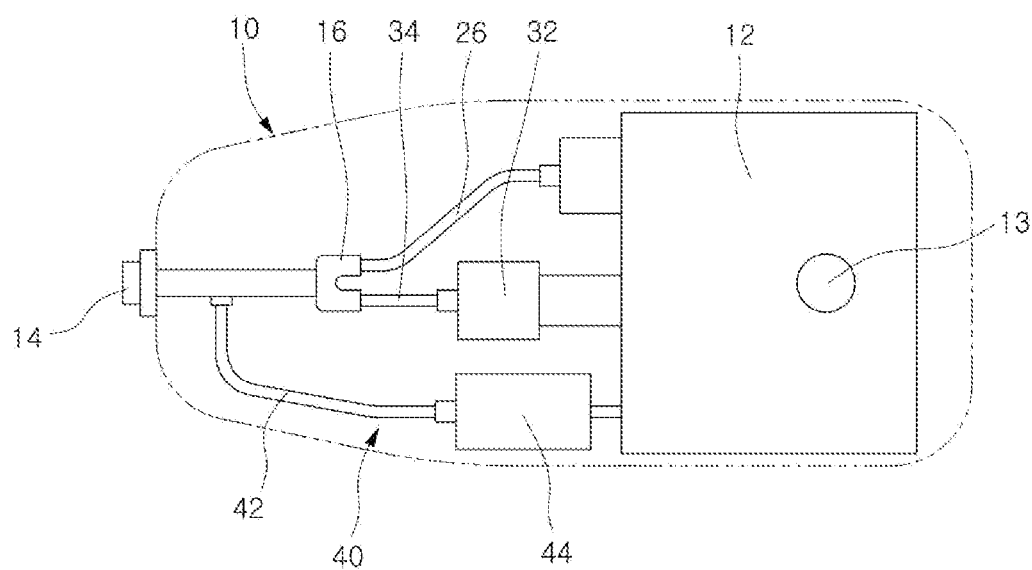
FIG. 3 is a plan view showing the water tank installed inside the portable sterilizer according to the present disclosure.

Referring to FIGS. 1 to 3, a portable sterilizer according to the present disclosure includes a housing 10, an ozone gas supply unit 20, a compressed air supply unit 30, a water supply unit 40, and a power supply unit 50.

The housing 10 is provided to form the exterior of the portable sterilizer according to the present disclosure, and includes a water tank 12, a nozzle 14, and a Y-shaped mixing tube 16.

The water tank 12 is installed inside the housing 10 and is formed to store a certain amount of water therein. A water inlet 13 exposed to the outside of the housing 10 is formed at the upper portion of the water tank 12. As the water inlet is exposed to the outside of the housing, it is possible to conveniently replenish water in the water tank. A water outlet (not shown) is formed in the lower portion of the water tank 12, and the water outlet is connected to the water supply hose 42 provided in the water supply unit 40.

The nozzle 14 is installed on one side of the housing 10 to be exposed to the outside. The housing 10 mixes ozone gas, compressed air, and water supplied from the ozone gas supply unit 20, the compressed air supply unit 30, and the water supply unit 40 and sprays them in a fog state. For this purpose, the nozzle 14 is formed as an atomizing nozzle.

Here, the atomizing nozzle mixes gas and liquid inside and sprays the liquid in a fog state with the power of compressed air. The structure of such an atomizing nozzle is a well-known technique widely practiced by those skilled in the art of a chemical liquid sterilizer or chemical liquid sprayer before the application of the present disclosure, and thus a description thereof will be omitted.

The Y-shaped mixing tube 16 is connected to one side of the nozzle 14. The ozone gas supply unit 20 is connected to the branched side of the Y-shaped mixing tube 16, and the compressed air supply 30 is connected to the other branched side of the Y-shaped mixing tube 16. The Y-shaped mixing tube 16 serves to mix the ozone gas supplied from the ozone gas supply unit 20 and the compressed air supplied from the compressed air supply unit 30 and supply the mixture to the nozzle 14. That is, the ozone gas of the ozone gas supply unit 20 and the compressed air of the compressed air supply unit 30 are mixed in the Y-shaped mixing tube 16 and then supplied to the nozzle.

The ozone gas supply unit 20 is provided to supply ozone gas to the nozzle 14, and includes an air pump 22, an ozone generator 24, and an ozone gas supply hose 26.

The air pump 22 sucks air and supplies the sucked air to the ozone generator 24. The ozone generator 24 generates ozone gas by mixing ozone and air sucked in by the air pump 22. For this purpose, the ozone generator 24 is formed of a known ozone generator. The ozone gas supply hose 26 is connected to the branched side of the Y-shaped mixing tube 16 so as to supply the ozone gas generated by the ozone generator 24 to the nozzle 14.

The ozone gas supply unit 20 configured as described above supplies the ozone gas generated by the air pump 22 and the ozone generator 24 to the branched side of the Y-shaped mixing tube 16 through the ozone gas supply hose 26.

The compressed air supply unit 30 is provided to supply compressed air to the nozzle 14, and includes a compression pump 32, and a compressed air supply hose 34.

The compression pump 32 generates compressed air and supplies the compressed air to the ozone generator 24. The compressed air supply hose 34 is connected to the other branched side of the Y-shaped mixing tube 16 so as to supply the compressed air generated by the compression pump 32 to the nozzle 14.

The compressed air supply unit 30 configured as described above supplies the compressed air generated by the compression pump 32 to the other branched side of the Y-shaped mixing tube 16 through the compressed air supply hose 34.

The water supply unit 40 is provided to supply the water stored in the water tank 12 to the nozzle, and includes a water supply hose 42 and an electric valve 44.

The water supply hose 42 is connected to a water outlet formed in the lower portion of the water tank 12. Accordingly, the water in the water tank 12 is supplied to the nozzle 14 by gravity.

The electric valve 44 is installed on the water supply hose 42. The electric valve 44 serves to regulate the flow of water supplied from the water tank 12 to the nozzle 14 through the water supply hose 42. To this end, the electric valve 44 is formed as a solenoid valve. That is, the electric valve 44 is opened and closed according to the control of a controller 52 to regulate the flow of water.

Figure 4:
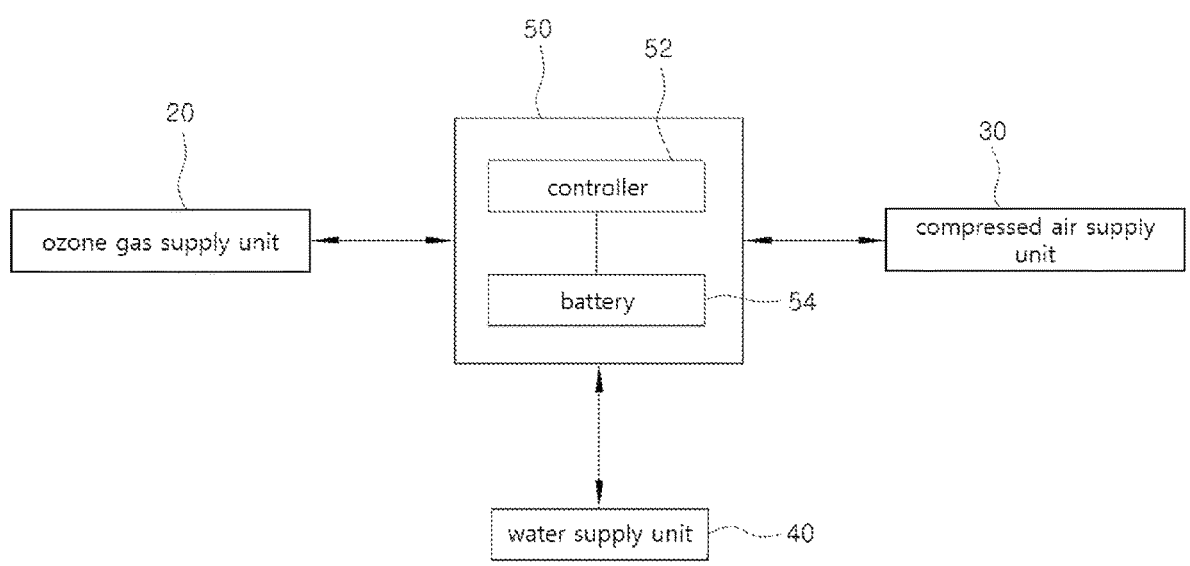
FIG. 4 is a block diagram showing a power supply state of the portable sterilizer according to the present disclosure.

Referring to FIG. 4, the power supply unit 50 is provided to supply power to the ozone gas supply unit 20, the compressed air supply unit 30, and the water supply unit 40, and includes the controller 52 and a battery 54.

The controller 52 supplies the power of the battery to the air pump 22 and ozone generator 24 of the ozone gas supply unit 20, the compression pump 32 of the compressed air supply unit 30, and the electric valve 44 of the water supply unit 40 when the portable sterilizer according to the present disclosure is in an ON state, and cuts off the power of the battery 54 when the portable sterilizer is in an OFF state.

The battery 54 is electrically connected to the air pump 22 and ozone generator 24 of the ozone gas supply unit 20, the compression pump 32 of the compressed air supply unit 30, and the electric valve 44 of the water supply unit 40 in order to apply or cut off power according to the control of the controller 52.

Hereinafter, the operating state of the portable sterilizer according to the present disclosure will be described.

First, during the ON operation of the portable sterilizer according to the present disclosure, the controller 52 controls the battery 54 to apply power to the ozone gas supply unit 20, the compressed air supply unit 30, and the water supply unit 40.

Then, the ozone gas supply unit 20 generates ozone gas by mixing air and ozone by the air pump 22 and the ozone generator 24, and the ozone gas is supplied to the branched side of the Y-shaped mixing tube 16 through the ozone gas supply hose 26. The compressed air supply unit 30 generates compressed air by the compression pump 32, and the compressed air is supplied to the other branched side of the Y-shaped mixing tube 16 through the compressed air supply hose 34. The compression pump 32 may supply air to the Y-shaped mixing tube 16 at a higher pressure than the air pump 22. The high-pressure air supplied by the compression pump 32 joins the ozone gas in the Y-shaped mixing tube 16 so that the ozone gas may be supplied to the nozzle 14 at a high pressure. At this time, by high pressure, water and ozone supplied from the nozzle 14 through the water supply hose 42 are mixed well, and the ozone water may be sprayed to the outside at high pressure through the nozzle 14 at the same time. When the air pump 22 supplies air to the ozone generator 24 at high pressure, the ozone generation efficiency of the ozone generator 24 may be lowered. Accordingly, the amount of dissolved ozone in the ozone water may decrease and the sterilization ability may be reduced. Therefore, the pressure of the air supplied by the air pump 22 should be appropriately selected in consideration of the ozone generation efficiency of the ozone generator 24, and in order to spray ozone water in the form of fog at high pressure well, it is preferable to add a compression pump 32 through a branch tube of the Y-shaped mixing tube 16 as before.

At the same time, the electric valve 44 of the water supply unit 40 is opened under the control of the controller 52, and the water in the water tank 12 is supplied to the nozzle 14 through the water supply hose 42.

The ozone gas and compressed air supplied to the Y-shaped mixing tube 16 are mixed inside the Y-shaped mixing tube 16 and supplied to the nozzle 14 in a mixed gas state, and the water in the water tank 12 is supplied directly to the nozzle 14.

The nozzle 14 finally mixes the mixed gas and water inside and sprays the sterilizing water in the fog state. That is, as the nozzle 14 is formed as an atomizing nozzle, the mixed gas and water may be sprayed with sterilizing water in a fog state.

The sterilizing water sprayed in the fog through the nozzle 14 contains ozone. Thus, it is possible to rapidly sterilize and disinfect surfaces as well as indoor objects exposed to a coronavirus without risk to public health.

As described above, the portable sterilizer according to the present disclosure may quickly sterilize and disinfect surfaces, indoor objects, and large areas exposed to coronavirus SARS-COV-2 by spraying ozone-containing sterilizing water in a fog state.

In the foregoing, specific embodiments of the present disclosure have been described and shown, but the present disclosure is not limited to the described embodiments, and it is apparent to those skilled in the art that various modifications and variations can be made without departing from the spirit and scope of the present disclosure. Accordingly, such modifications or variations should not be understood as separate from the technical spirit or point of view of the present disclosure, but should be considered to belong to the claims of the present disclosure.

Description of Numerals

10: housing
12: water tank
14: nozzle
16: Y-shaped mixing tube
20: ozone gas supply unit
22: air pump
24: ozone generator
26: ozone gas supply hose
30: compressed air supply unit

32: compression pump
34: compressed air supply hose
40: water supply unit
42: water supply hose
44: electric valve
50: power supply unit
52: controller
54: battery

The invention claimed is:

1. A portable sterilizer, comprising:
a housing in which a water tank is installed inside;
a nozzle capable of spraying sterilizing water in a fog state is installed to be exposed to an outside on a side thereof;
a Y-shaped mixing tube connected to the nozzle;
an ozone gas supply unit including an air pump, installed inside the housing and connected to a first branched side of the Y-shaped mixing tube and configured to supply ozone gas to the nozzle;
a compressed air supply unit installed inside the housing and connected to a second branched side of the Y-shaped mixing tube and configured to supply compressed air to the nozzle, wherein the compressed air is supplied through the other end of said Y-shaped mixing tube by a compression pump providing a pressure greater than the pressure of said air pump; and
a water supply unit installed inside the housing and configured to supply water from the water tank to the nozzle,
wherein the ozone gas and compressed air are supplied to the nozzle in a mixed gas state, the water is supplied directly to the nozzle, and the mixed gas and water are finally mixed inside the nozzle and then sprayed with sterilizing water in a fog state,
wherein the ozone gas and compressed air are mixed by the Y-shaped mixing tube and supplied to the nozzle as a mixed gas,
wherein the water supply unit comprises: a water supply hose configured to connect the water tank and the nozzle and an electric valve installed on the water supply hose and configured to regulate a flow of water supplied from the water tank to the nozzle.

2. The portable sterilizer of claim 1, wherein the ozone gas supply unit comprises:
an ozone generator that generates ozone gas by mixing the air and ozone generated by the air pump; and
an ozone gas supply hose connected to the first branched side of the Y-shaped mixing tube to supply the ozone gas generated by the ozone generator to the nozzle.

3. The portable sterilizer of claim 1, wherein the compressed air supply unit comprises:
a compressed air supply hose connected to a second branched side of asaid Y-shaped mixing tube to supply the compressed air generated by the compression pump to the nozzle.

4. The portable sterilizer of claim 1, further comprising:
a power supply unit for supplying power to the ozone gas supply unit, the compressed air supply unit, and the water supply unit, wherein the power supply unit is composed of a controller and a battery.

5. The portable sterilizer of claim 1, wherein the nozzle is configured as an atomizing nozzle so as to mix the mixed gas and water.

* * * * *